United States Patent
Delache et al.

(10) Patent No.: US 9,983,039 B2
(45) Date of Patent: May 29, 2018

(54) FLOW SENSING DEVICE WITH TEMPERATURE COMPENSATION

(75) Inventors: Alain-Jean Delache, Nice (FR); Steven Adam Kimmel, Delmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 946 days.

(21) Appl. No.: 13/508,638

(22) PCT Filed: Oct. 15, 2010

(86) PCT No.: PCT/IB2010/054683
§ 371 (c)(1),
(2), (4) Date: May 8, 2012

(87) PCT Pub. No.: WO2011/055254
PCT Pub. Date: May 12, 2011

(65) Prior Publication Data
US 2012/0226449 A1    Sep. 6, 2012

(30) Foreign Application Priority Data
Nov. 9, 2009    (EP) ..................... 09306069

(51) Int. Cl.
*G01F 1/30* (2006.01)
*G01F 1/36* (2006.01)
(Continued)

(52) U.S. Cl.
CPC ....... *G01F 15/024* (2013.01); *A61M 16/0066* (2013.01); *A61M 16/0858* (2014.02);
(Continued)

(58) Field of Classification Search
CPC ..... G01F 1/34; G01F 1/36; G01F 1/42; G01F 1/44; G01F 1/50
(Continued)

(56) References Cited

U.S. PATENT DOCUMENTS 4,651,292 A * 3/1987 Jeenicke ............. G01L 19/0092
702/104
5,766,130 A * 6/1998 Selmonosky ........ A61B 5/1073
600/485
(Continued)

FOREIGN PATENT DOCUMENTS

FR    2615618 A1    11/1988
WO    WO0138832 A2    5/2001

OTHER PUBLICATIONS

Hugo Chueng and Sreeja Raj, "Implentation of 12-Bit Delta-Sigma DAC with MSC12xx controller", 2005, Publisher TI, p. 1.*
(Continued)

*Primary Examiner* — Michael Dalbo
(74) *Attorney, Agent, or Firm* — Michael W. Haas (57) ABSTRACT

A device (12) that uses a temperature coefficient pre-calibrated for the device for measuring a flow within the device. The device includes a differential pressure sensor (80) configured to generate a differential pressure signal responsive to a differential pressure within a flow path (16) and a temperature sensor configured to sense a temperature near the differential pressure sensor. A differential amplifier amplifies differential pressure signals from the differential pressure sensor. A processor receives signals from the differential pressure sensor, amplified signals from the differential amplifier, and signals from the temperature sensor. The amplified signals are corrected based upon at least a predetermined temperature coefficient, and the processor calculates a flow rate based on the corrected representation of the differential pressure.

9 Claims, 6 Drawing Sheets (51) Int. Cl.
*G01F 1/42* (2006.01)
*G01F 1/50* (2006.01)
*A61M 16/00* (2006.01)
*G01F 15/02* (2006.01)
*G01F 15/04* (2006.01)
*G01F 25/00* (2006.01)
*A61M 16/08* (2006.01)
*G01F 1/44* (2006.01)

(52) U.S. Cl.
CPC .............. *G01F 1/36* (2013.01); *G01F 15/046* (2013.01); *G01F 25/0007* (2013.01); *A61M 2016/0039* (2013.01); *G01F 1/42* (2013.01); *G01F 1/44* (2013.01); *G01F 1/50* (2013.01)

(58) Field of Classification Search
USPC ..................................................... 702/47, 98
See application file for complete search history.

(56) References Cited

U.S. PATENT DOCUMENTS

| | | | |
|---|---|---|---|
| 7,554,666 B2 | 6/2009 | Russell | |
| 7,654,146 B2 | 2/2010 | Orr | |
| 2002/0173899 A1* | 11/2002 | Miller | F02D 41/2474 701/108 |
| 2004/0144178 A1* | 7/2004 | Ohmi | G01D 3/022 73/708 |
| 2004/0154383 A1 | 8/2004 | Woolf | |
| 2004/0159099 A1* | 8/2004 | Kuboshima | F01N 9/002 60/297 |
| 2004/0211423 A1* | 10/2004 | Baecke | 128/204.23 |
| 2005/0029453 A1* | 2/2005 | Allen | G01J 5/06 250/332 |
| 2005/0121033 A1* | 6/2005 | Starr | A61M 16/1065 128/204.18 |
| 2005/0217250 A1* | 10/2005 | Kuboshima | F01N 9/002 60/287 |
| 2007/0047928 A1* | 3/2007 | Ogino | H02P 6/165 388/804 |
| 2009/0025368 A1* | 1/2009 | Sakimoto | B01F 3/04049 60/285 |
| 2009/0320836 A1* | 12/2009 | Baker, Jr. | A61M 16/12 128/203.14 |
| 2011/0162647 A1* | 7/2011 | Huby | A61M 16/0057 128/203.14 |

OTHER PUBLICATIONS

"Intelligent Temperature Monitor and PWM Fan Controller", 2007, Publisher TI, p. 1.*
Rick Jeffs, Scott Holden and Dennis Bohn, "Dynamic Processors", 2005, Rane Corporation, Chapters 1 and 3.*

* cited by examiner

FLOW SENSING DEVICE WITH TEMPERATURE COMPENSATION

CROSS-REFERENCE TO RELATED APPLICATIONS

The invention relates to devices used for the measurement of flow, and, in particular, to a flow sensing device that uses a temperature coefficient pre-calibrated for the device.

BACKGROUND OF THE INVENTION

1. Field of the Disclosure

Respiratory flow measurement during the administration of anesthesia, in intensive care environments, and in monitoring the physical condition of athletes and other individuals prior to and during the course of training programs and other medical tests provides valuable information for assessment of cardiopulmonary function and breathing circuit integrity.

2. Description of the Related Art

Differential pressure measurement devices such as flow meters have conventionally been used to obtain respiratory flow measurements. One use of differential pressure measurement devices is in CPAP (Continuous Positive Airway Pressure) therapy, which may be used to treat obstructive sleep apnea (OSA). CPAP is used to hold the air pressure in a person's airway at a constant level which is just slightly above the atmospheric pressure (at an exact pressure level which is prescribed by a doctor) so that the collapsing airway is splinted open by the added air pressure. This pressure level is ideally held constant no matter what point the person is in his/her breathing cycle. However, some patients feel discomfort when exhaling against the added pressure and as a result, may give up on the therapy entirely. For these patients, their low compliance with CPAP therapy can be enhanced with the addition of any of various known forms of pressure relief.

To deliver pressure relief, a pressure support device should properly determine when the patient is exhaling, and manipulate the amount of air pressure which is delivered to the patient's airway in proper synchrony with the patient's entire breathing cycle. The pressure support device obtains measurements of the flow rate using differential pressure measurement devices so that the correct amount of pressure relief can be delivered to the patient. Differential pressure measurement devices may also be used in other machines, such as ventilators, automotive engines, and combustion engines, or any devices that utilize flow.

In some differential pressure measurement devices, flow rate Q is calculated in accordance with the formula $Q=K*\sqrt{(\Delta P)}$ when $\Delta P>=0$, and $Q=-1*K*\sqrt{(-1*\Delta P)}$ when $\Delta P<0$, where Q is the air flow rate, $\Delta P$ is the pressure drop across an orifice (or pressure differential) of a flow restriction, and K is an appropriate constant of proportionality. Typically, a pressure sensor is operatively coupled with the restriction to sense the differential pressure across the restriction. Because of the nonlinearity of the equations mentioned above, the system can "see" or resolve much smaller variations in flow when the flow is above a predetermined threshold as compared to what it can "see" or resolve when the flow is below a predetermined threshold (e.g., at or near zero). That is, the resolution of the flow signals is much better for flows above a predetermined threshold than for flows below the predetermined threshold. Thus, when the flow is below a predetermined threshold value, such as near zero, there may be a lack of adequate resolution in the flow signals.

SUMMARY OF THE INVENTION

One aspect of the invention is related to a device that uses a temperature coefficient pre-calibrated for the device for measuring a flow within the device. The device includes a flow path and a flow restriction portion disposed in the flow path that creates a differential pressure within the flow path. The device also includes a differential pressure sensor configured to generate a differential pressure signal responsive to the differential pressure within the flow path and a temperature sensor configured to sense a temperature at or near the differential pressure sensor. The device further includes a differential amplifier that amplifies differential pressure signals from the differential pressure sensor. The device also includes a processor that receives signals from the differential pressure sensor including the amplified signals from the differential amplifier. The amplified signals are corrected based upon a predetermined temperature coefficient. The processor calculates a flow rate based on the signals from the differential pressure sensor.

Another aspect of the invention provides a device that uses a temperature coefficient pre-calibrated for the device for measuring a flow within the device. The device includes a flow path and a flow restriction portion disposed in the flow path that creates a differential pressure within the flow path. A differential pressure sensor in the device is configured to generate a differential pressure signal based upon the differential pressure within the flow path. A temperature sensor in the device is configured to sense ambient temperature at or near the differential pressure sensor. The device also includes a processor configured to generate pulse width modulated signals.

The pulse width modulated signals have a duty cycle that varies based on the predetermined temperature coefficient, a sensed first differential pressure from the differential pressure sensor, a sensed first temperature from the temperature sensor, and a sensed second temperature from the temperature sensor. The first differential pressure and the first temperature are sensed before flow through the device is generated. The device also includes a differential amplifier that receives second differential pressure signals from the differential pressure sensor reflective of a sensed second differential pressure and also receives the pulse width modulated signals, wherein the differential amplifier outputs difference signals based on an amplified difference between the second differential pressure signals and the pulse width modulated signals, and wherein the second differential pressure and the second temperature are sensed after the first temperature and the first differential pressure have been sensed. The device also includes an A-D converter for receiving the amplified difference signals from the differential amplifier arrangement and the second differential pressure signals and digitalizing the amplified difference and the second differential pressure signals for transmission to the processor. The processor calculates the flow using the digitalized amplified difference signals and/or the digitalized second differential pressure signals from the A-D converter.

Another aspect provides a method for using a temperature coefficient pre-calibrated for a device that measures flow. The method includes the step of creating a differential pressure within the flow path and using a differential pressure sensor to generate a differential pressure signal based upon the differential pressure within the flow path. The method further includes the step of sensing a temperature at or near the differential pressure sensor and amplifying at least a portion of the differential pressure signals from the differential pressure sensor. The method also includes the step of calculating a flow rate based on the signals from the differential pressure sensor. The amplified signals are corrected based upon a predetermined temperature coefficient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

In flow measurement embodiments that use an A-D converter with limited analog to digital converter resolution to digitalize the differential pressure signals for transmission to a processor, a one-bit or one-count change in the pressure level may correspond to large flow differences at low flows, thus leading to poor flow reading accuracy at low flows as discussed above. To more accurately measure the pressure drop through a restriction produced from flows that are below the predetermined threshold, the signal from a differential pressure transducer sensing the pressure must be amplified to allow accurate readings. However, when the signals from the differential pressure transducer are amplified, so are the effects of thermal drift. That is, the output reading of the differential pressure transducers may vary from the actual differential pressure within the flow restriction because of internal heating of the equipment during normal operation or by changes in external ambient temperature. With respect to CPAP therapy, this can lead to inaccuracies which may manifest themselves in errors in the timing of the delivery of pressure relief and in the amount of pressure relief which is ultimately delivered. The temperature compensation system and method disclosed herein can be used to alleviate some or all of these issues.

Figure 1:
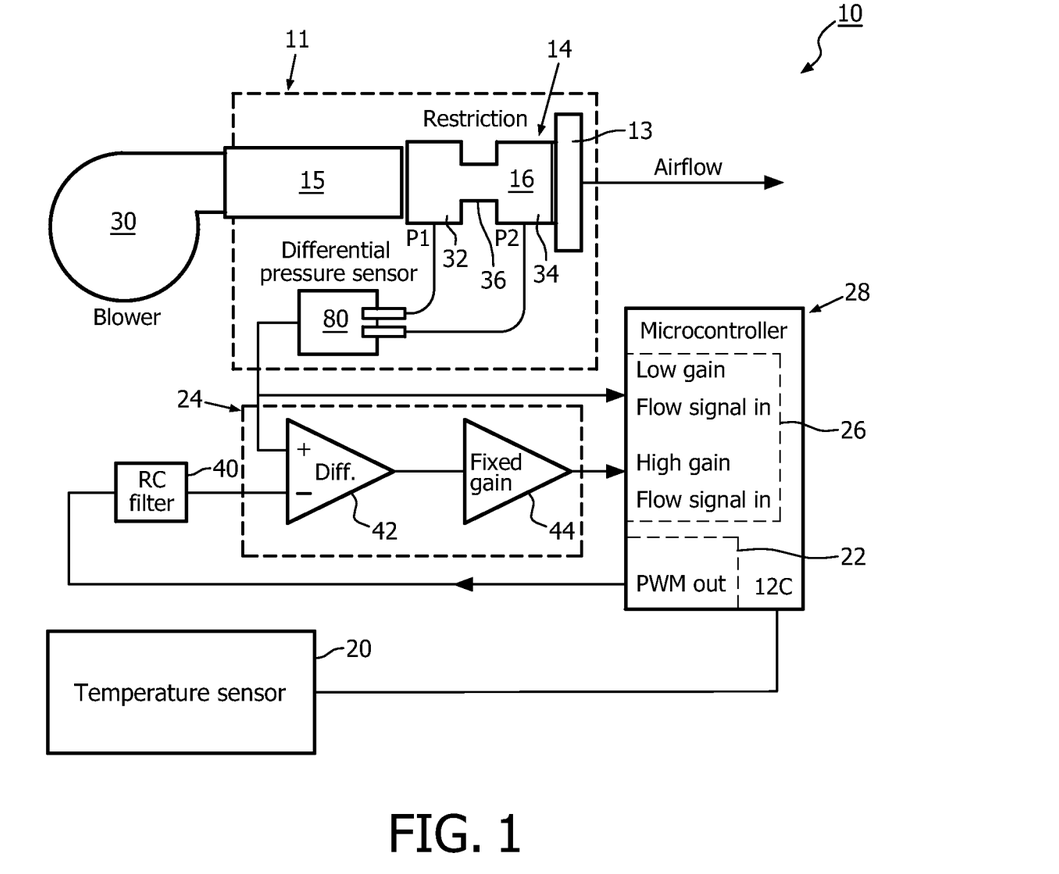
FIG. 1 is a schematic diagram of a flow measuring system of a device in accordance with an embodiment.

FIG. 1. schematically shows an exemplary embodiment of a flow measuring system 10 used in a device 12 (see FIG. 8), such as for example, a CPAP device, wherein a temperature compensation coefficient is pre-calibrated for each individual device for measuring flow in the device 12. Flow measuring system 10 of device 12 includes a flow sensing system 11 having a flow restriction portion 14 disposed in a flow path 16 that creates a pressure differential or pressure drop within flow path 16. Device 12 also includes a differential pressure sensor 80 configured to sense the differential pressure created by flow restriction portion 14.

Flow restriction portion 14 may include an obstruction 36 that blocks a portion of the flow of respiration or other gases or gas mixtures along the flow path 16 and positioned at least partially between pressure port 32 and pressure port 34 to create a pressure differential in the gas flow therebetween. Flow restriction portion 14 and/or obstruction 36 may be formed from an inexpensive, readily mass-producible material, such as an injection moldable plastic. In some embodiments, pressure sensor 80 and flow restriction portion 14 may be of the type described in U.S. patent application Ser. No. 11/805,074, which is hereby incorporated by reference in its entirety. Other embodiments of pressure restrictions and pressure sensors may also be used, such as, for example, those described in U.S. patent Ser. No. 11/705,561, which is hereby incorporated by reference in its entirety.

Figure 2:
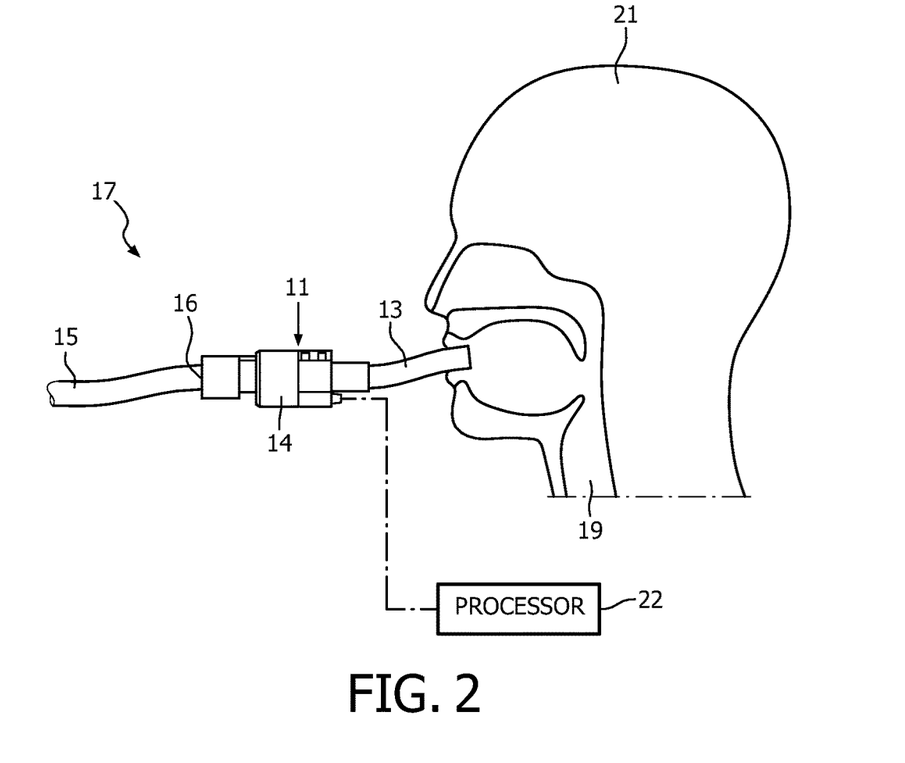
FIG. 2 illustrates a respiratory circuit including an airway adaptor carrying sensors operatively coupled to a processor, in accordance with one embodiment of the invention.

FIG. 2 shows flow sensing system 11 disposed in a portion of a respiratory circuit 17 according to one embodiment of the invention. Respiratory circuit 17 includes, among other things, a first end 13, a second end 15, and flow restriction portion 14. First end 13 of respiratory circuit 17 is adapted to deliver the flow of gas to a patient. For example, first end 13 of respiratory circuit 10 may include a patient interface appliance configured to communicate with an airway 19 of patient 21. Some examples of the patient interface appliance may include, for example, an endotracheal tube, a tracheotomy tube, a mask, or other patient interface appliances. Second end 15 of respiratory circuit 17 is configured to communicate with a source of gas 30 (see FIG. 1). For instance, the source of gas 30 may include ambient atmosphere, a wall gas, a blower, or other sources of gas.

Referring back to FIG. 1, the flow sensing system 11 includes flow path 16 and two pressure ports 32 and 34 that are in communication with the flow path. Differential pressure sensor 80 senses the differential pressure based on the difference in pressures from ports 32 and 34. Differential pressure sensor 80 transmits a signal that is reflective of the sensed differential pressure. In one embodiment, differential pressure sensor 80 may include a bridge circuit comprised of an array of resistors and which is capable of monitoring the differential pressure. For example, differential pressure sensor 80 may include a silicon diaphragm having piezo resistors that comprise an electrical bridge whose output is analogous to the differential pressure applied to the differential pressure sensor. Other types of differential pressure sensor 80 may optionally be used.

In this embodiment, flow measuring system 10 of device 12 also includes a temperature sensor 20 configured to sense the temperature at or near the differential pressure sensor 80.

The temperature surrounding or at differential pressure sensor 80 may impact the output reading of the differential pressure sensor, which will also be referred to herein as the differential pressure reading. Therefore, temperature sensor 20 is placed at or near differential pressure sensor 80 to measure the ambient temperature or physical temperature at or near the differential pressure sensor so that this measurement may be used to compensate for thermal drift, which will be described in more detail later.

In one embodiment, temperature sensor 20 may be a thermistor, although other temperature sensors can be used, such as, for example, a thermometer, thermopile, or other temperature sensing devices. Temperature sensor 20 may be an embedded feature within a microcontroller 28 and whose temperature could be read by a processor 22 through I²C (Inter-Integrated Circuit) communications. In some embodiments, temperature sensor 20 is separately and operatively connected to microcontroller 28.

Processor 22 is also configured to calculate flow rate using the differential pressure sensed by the differential pressure sensor 80 and the temperature compensation coefficient pre-calibrated for device 12. Processor 22 may also include a pulse width modulator that modulates signals for transmission through a differential amplifier or differential amplifier arrangement 24. The duty cycle of the pulse width modulated signals may vary based on the pre-calibrated temperature compensation coefficient and readings from the differential pressure sensor and the temperature sensor, which will be described in more detail later. The use of the pulse width modulation signals to compensate for thermal drift will be hereinafter referred to as "coarse adjustment" or "coarse correction" and will also be described in more detail later. As used herein, the terms "compensate" and "compensation" are not limited to the addition of values, subtraction of values, percentage of values, or any mathematical relationship or formulation of values.

In one embodiment, microcontroller 28 may include processor 22 and conversion apparatus 26, although these components may optionally be provided separately. Conversion apparatus 26 takes the form of an A-D converter in this embodiment. Although processor 22 is shown to be located on the microcontroller 28 in this embodiment, the processor that calculates the flow, or other components of microcontroller 28, may optionally be located on another controller or unit in device 12. In addition, the optional collection of microcontrollers or devices can, for the purposes of this disclosure, be considered to be a single microcontroller or device, although components thereof may be provided separately and operatively interconnected. In some embodiments where components are separately and operatively interconnected, the transmission of signals may be made along, just for example, a computer communication cable or by wireless transmission, such as infrared transmission. Furthermore, the components of flow measuring system 10 are not intended to be limiting and the various components mentioned above may be part of other systems.

The electrical analog signal from differential pressure sensor 80 is transformed in the A/D converter 26 to a digital signal for input into the processor 22. Processor 22, under control of one or more programs in the form of software or firmware, may then, based on the signals received thereby, employ known principles and algorithms to calculate respiratory flow.

The A/D converter 26 may include a "low gain channel" and a "high gain channel." As mentioned above, when differential pressure signals are digitalized for transmission to the processor 22 using an A-D converter with limited analog to digital converter resolution, a one-count change in the pressure level may correspond to large flow differences at low flows, thus leading to lower accuracy at low flows. As such, when the flow is low, a higher gain is used on the differential pressure signals to establish adequate resolution. In other words, to accurately measure the differential pressure produced from low flow through the restriction 14, the signal from the differential pressure sensor 80 must be amplified to allow more accurate readings.

Figure 3:
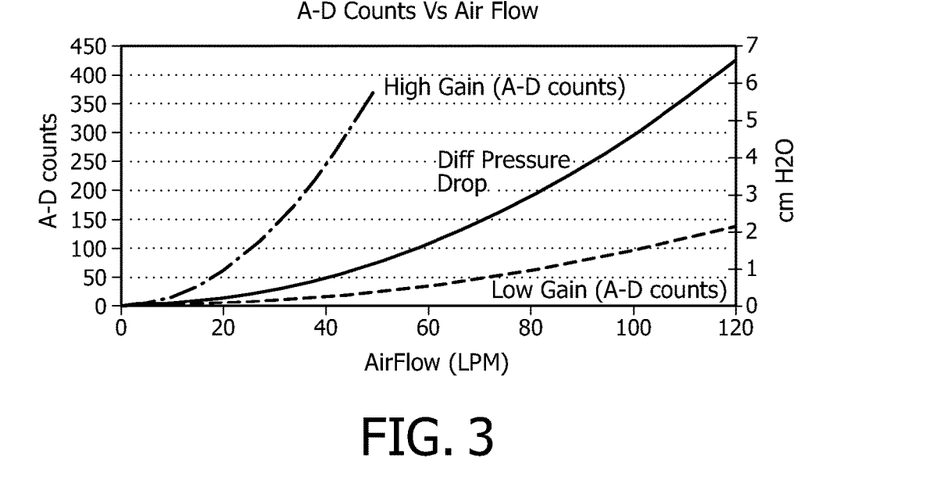
FIG. 3 is a graph showing the flow rate as a function of A-D counts.

As shown in FIG. 3, when the "high gain channel" is used for flows below a predetermined flow rate threshold, such as, for example, below 45 LPM (liters per minute), each A-D count corresponds to a smaller flow difference. However, as also shown in FIG. 3, the "high gain channel" cannot be used for flow rates above the predetermined flow rate threshold because the signals "rail" or "plateau." On the other hand, the "low gain channel" may be used for flow rates above 45 LPM in this embodiment. The "low gain channel" corresponds to gains that are set so that the maximum expected range results in signals that will fit within the input range of A-D converter's 26 input.

In one embodiment, the differential pressure readings will go into A-D converter 26 through both the low gain channel and the high gain channel. Processor 22 may select which signals to use for the air flow rate calculation—the signals received from the low gain channel or the signals received from the high gain channel, or a combination thereof. The selection may depend upon the range of the signals received and the resolution. For example, in one embodiment, processor 22 may analyze the signals received from the low gain channel first. However, if the resolution is determined by the processor to be outside the lower gain (high flow) region, or otherwise to be inadequate, the signals from the high gain channel may be used.

As shown in FIG. 1, device 12 also includes differential amplifier arrangement 24 for amplifying signals relating to the differential pressure below a predetermined threshold and conversion apparatus 26 for converting the signals generated by the first sensor for transmission to processor 22. Differential amplifier arrangement 24 may include differential amplifier 42 and fixed gain amplifier 44, although it is also contemplated that the differential amplifier arrangement 24 may optionally just be one differential amplifier component that amplifies the difference between input signals. Differential amplifier 42 may be configured to output a signal reflective of the difference between two input signals. In some embodiments, differential amplifier 42 may also be used to amplify the output signals. Fixed gain amplifier 44 may have a predetermined gain stage that may be used to amplify or increase the signals received from differential amplifier 42. In some embodiments, fixed gain amplifier 44 may increase the signals by a factor of 10, 100, or other values.

Although differential amplifier 42 and fixed gain amplifier 44 are two components in this embodiment, it is contemplated that the differential amplifier and the fixed gain amplifier together may be considered to be one differential amplifier in other embodiments. That is, in addition to receiving two input signals and transmitting the difference between the signals, the differential amplifier could also amplify the difference between the signals before transmitting the difference between the signals. The output of differential amplifier arrangement 24 is an amplified output of the difference between the signal coming from differential pressure sensor 80 and the pulse width modulated signal from processor 22.

RC filter 40 may be operatively connected to the differential amplifier arrangement 24 and may be configured to convert modulated (or pulse width modulated) signals received from processor 22 to DC signals. That is, RC filter 40 may be used to convert the digital signals from the processor 22 to analog signals for input into differential amplifier 42. RC filter 40 may accomplish this, for example, by transmitting an average value of the pulse train of the pulse width modulated signals received from processor 22 to the differential amplifier 42. RC filter 40 may also be used to remove noise or other signal artifacts. In some embodiments, a converter (not shown), such as a digital to analog converter, is operatively connected to processor 22 and used to convert the digital signals from the processor into analog signals to be received by differential amplifier 42. In some embodiments, the digital to analog converter is located on the microcontroller 28. In some embodiments, the digital to analog converter is separately and operatively connected to microcontroller 28.

As mentioned above, the "high gain channel" corresponds to signals that are "boosted" or amplified so that a more accurate flow rate can be obtained when the flow or differential pressure is near zero. However, when the signals from the differential pressure sensor 80 are amplified, the effects of thermal drift are also amplified. As such, a temperature compensation coefficient can be used to extract a more accurate flow calculation.

In one embodiment, a predetermined temperature coefficient can be obtained experimentally and programmed into all devices 12 (best coefficient or average coefficient used for all devices 12 based on experimentation). In another embodiment, a temperature compensation coefficient may be obtained or calibrated for each individual device 12. That is, a device 12 may have its own individual temperature compensation coefficient stored in an electronic storage device, such as a memory (not shown) on the microcontroller 28. The temperature compensation coefficient may optionally be obtained during a "run-in" period where newly assembled units are "run-in" for a period of time to properly distribute lubricant in motor bearings and potentially weed out any initial problems in electronic control circuitry.

In some embodiments, to obtain the temperature coefficient, a first differential pressure reading and a first temperature are measured at the beginning of the "run-in" period, also known as a "cold condition". In such embodiments, a second differential pressure reading and a second temperature are obtained at the end of the "run-in" period, also known as a "hot condition." The output from the first pressure differential (or first pressure differential reading) and first temperature and the output from the second differential pressure (or second differential pressure reading) and second temperature may be obtained when flow is generated through device 12, such as when the first pressure reading and the second pressure reading are obtained at the same actual pressure differential or flow in the device. For example, in some embodiments, the first pressure reading and the first temperature are obtained at a first pressure drop across the flow restriction 14 (e.g., at a start-up or cold temperature). Differential pressure sensor 80 is then heated for a period of time until the temperature is stabilized. Differential pressure sensor 80 may be heated, just for example, by operating device 12 (with the blower 30 operating) for a period of time. The second pressure reading and the second temperature are obtained after the period of time and while the pressure drop across the flow restriction 36 is the same as when the first differential pressure reading was obtained (the first pressure drop). In one embodiment, the first pressure drop and second pressure drop may be zero, or some other same pressure drop.

Figure 4:
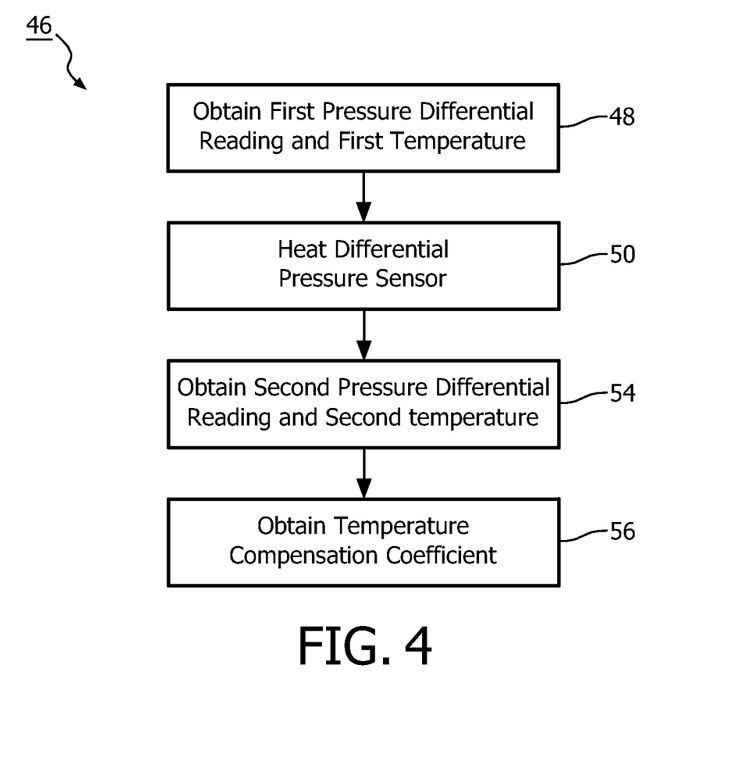
FIG. 4 is a flow chart illustrating a method of calibrating the device to obtain a temperature compensation coefficient in accordance with an embodiment.

FIG. 4 illustrates one method 46 of calibrating a specific device 12 to obtain the temperature compensation coefficient in accordance with one embodiment. Method 46 starts at procedure 48 wherein the first differential pressure reading is obtained using differential pressure sensor 80 and the first temperature is measured by temperature sensor 20. The first differential pressure reading is obtained using the differential pressure sensor 80 at a first pressure drop across flow restriction portion 14. In one embodiment, this procedure 48 is performed before the blower 30 is turned on and before device 12 is operated, and in other words, the pressure drop across the flow restriction 14 is zero (and hence the flow is zero). In some embodiments, these measurements may be taken at the beginning of the "run-in" period with the "cold condition." Device 12 may store these measurements in its memory.

Method 46 then proceeds to procedure 50, wherein differential pressure sensor 80 is heated for a period of time until the temperature near the differential pressure sensor is stabilized. In some embodiments, the heating is accomplished by running device 12. Specifically, device 12, including blower 30, is turned on and flow is generated through the device. The device (and the blower 30) may be operated, such as, for example, for an hour, two hours, or any other time interval that will heat the device. For example, device 12 may be heated until it reaches a stable temperature. The device is then turned off. As a result of the heating, the electronic components of the device are warmed so that the temperature at or near the components are increased.

Method 46 proceeds to procedure 54 wherein the second differential pressure reading is obtained using differential pressure sensor 80 and the second temperature is measured using temperature sensor 20. The second differential pressure reading is obtained while the pressure drop across the flow restriction 14 is the same as that when the first pressure reading was obtained. For example, the second differential pressure reading can be obtained when flow has been discontinued through the 12 so that the pressure drop is zero. In some embodiments, these measurements may be performed at the end of the "run-in" period or the "hot condition." Method 46 then proceeds to procedure 56 wherein the temperature compensation coefficient is obtained. The temperature compensation coefficient may be calculated using the following equation $$TempCo = \frac{(\Delta P_1 - \Delta P_0)}{(T_1 - T_0)}, \quad \text{(Equation 1.1)}$$

where:
TempCo=temperature compensation coefficient,
$\Delta P_1$=second differential pressure reading from differential pressure sensor,
$\Delta P_0$=first differential pressure reading from differential pressure sensor,
$T_1$=second temperature value, and
$T_0$=first temperature value.

The temperature coefficient TempCo will be a temperature compensation value that will be reflective of a variance in the output reading from differential pressure sensor 80 when the sensor has been heated (thus causing thermal drift in the output reading).

As noted previously, in one embodiment, the first differential pressure value, the second differential pressure value, the first temperature and the second temperature are obtained when the blower is off (when the flow generated through the device is zero). The second differential pressure value and the second temperature are obtained after device 12 has been operated for a certain time interval, which may be sufficient for significant warming of the devices to occur. After each device 12 is put into a calibration mode wherein method 46 is performed, each device may have its own pre-calibrated temperature compensation coefficient to be applied later to the output of the differential pressure sensors 80 to compensate for thermal drift.

In another embodiment, the first and second readings can be taken at a predetermined constant pressure drop other than zero.

After the temperature compensation coefficient has been obtained, the temperature compensation coefficient may be stored in a memory in each device 12 for later use to compensate the differential pressure output of the differential pressure sensor 80 for thermal drift.

Figure 5:
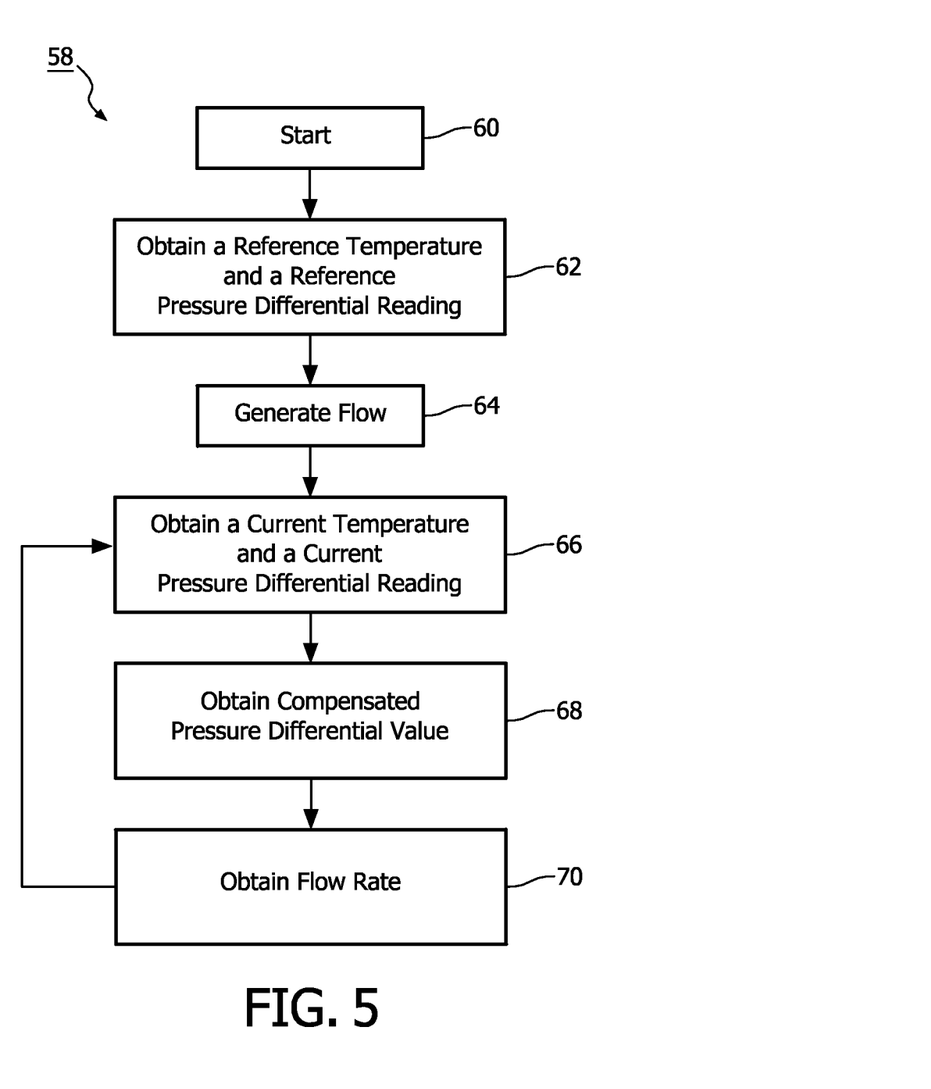
FIG. 5 is a flow chart illustrating a method of implementing the temperature compensation coefficient in accordance with an embodiment.

FIG. 5 shows a method 58 of implementing the temperature compensation coefficient to compensate the differential pressure output of the differential pressure sensor 80 in accordance with one embodiment. Method 58 starts at procedure 60 wherein device 12 auto-nulls its sensors, including differential pressure sensor 80. This may be performed before flow is generated through the flow path by blower 30. Method 58 then proceeds to procedure 62 wherein a first differential pressure reading or reference differential pressure reading is obtained using differential pressure sensor 80. A first temperature or reference temperature is also obtained using the temperature sensor 20 during this procedure. In this embodiment, procedure 62 is performed before flow is generated through device 12 (before blower 30 is turned on).

Method 58 then proceeds to procedure 64 wherein flow is generated through the device 12 (after the blower is turned on) during regular use. Method 58 then proceeds to procedure 66 wherein a second temperature is measured using the temperature sensor 20. The second temperature may be higher, equal to, or lower than the reference temperature. In some situations, the second temperature may be lower due to lower ambient or room temperature during the night. During this procedure 66, a second differential pressure reading or raw differential pressure reading is also obtained using the differential pressure sensor 80. The raw differential pressure reading may also be referred to as the current differential pressure reading, which is the differential pressure reading that will be compensated for thermal drift for the calculation of the flow rate. As such, procedure 66 may be performed during therapy, when flow is provided to the patient.

Method 58 then proceeds to procedure 68 wherein the compensated differential pressure value is obtained using the following equation (Equation 1.2):

$$\Delta P_{Comp} = \Delta P_{Raw} - [\Delta P_{Ref} + \text{TempCo}*(T_1 - T_{Ref})],$$

where:
$\Delta P_{Comp}$ = compensated differential pressure,
$\Delta P_{Raw}$ = raw differential pressure value,
$\Delta P_{Ref}$ = reference differential pressure value,
TempCo = temperature compensation coefficient (obtained from Equation 1.1 shown above),
$T_1$ = second temperature value (or current temperature value), and
$T_{Ref}$ = reference temperature value, The expression or term $\Delta P_{Ref} + \text{TempCo}*(T_1 - T_{Ref})$ found inside the brackets of the equation mentioned above will be hereinafter referred to as "compensation value." The compensation value is the estimated output reading of the differential pressure sensor 80 at zero flow (if the temperature coefficient was obtained at zero flow) at the second temperature $T_1$. Thus, by subtracting the compensation value from the raw differential pressure value, the differential pressure value compensating for the thermal drift (the compensated differential pressure value) is obtained. The method 58 then proceeds to procedure 70 wherein the flow rate is obtained using the compensated differential pressure value. The flow rate may be obtained using the following equation (Equation 1.3):

$$Q = K*\sqrt{\Delta P_{Comp}} \text{ when } \Delta P_{Comp} \geq 0, \text{ and}$$

$$Q = -1*K*\sqrt{-1*\Delta P_{Comp}} \text{ when } \Delta P_{Comp} < 0,$$

where:
Q = flow rate (e.g., liters per minute),
K = constant of proportionality, and
$\Delta P_{Comp}$ = compensated differential pressure value.

Method 58 may then proceed back to procedure 66 to obtain the second differential pressure at another time period. Procedure 66 may be performed at regular intervals or at any time during use of device 12. After each time that procedure 66 is performed, the method 58 may then proceed to procedures 68 and 70. This enables the continuous measuring of the ambient temperature and the continuous temperature compensation of the raw differential pressures to obtain flow rates. Procedure 62 may be performed periodically at a predetermined time interval or at any time, such as right after device 12, including blower 30, is turned off.

The above mentioned equation, Equation 1.3, assumes that the output of differential pressure sensor 80 changes linearly with temperature. However, in situations where the output of the differential pressure sensor does not change linearly with temperature, that is, the effect of thermal drift is not linear relative to temperature, the "compensation value" may optionally be replaced with a non-linear approximation. The compensation value is not limited to the linear expression mentioned above. The "compensation value" may optionally be obtained by using a lookup table (based on temperature).

In some embodiments, in order to extract the correct flow rate (the flow rate that has been compensated or corrected for thermal drift) from the differential pressure sensor 80, the value of the output of differential pressure sensor 80 when no flow is generated is required. Equation 1.3 enables the calculation of the output of differential pressure sensor 80 (or the differential pressure reading) when no flow is generated. Specifically, the temperature compensation coefficient, the reference differential pressure reading, the reference temperature, and the second temperature enables the calculation of the output of the differential pressure sensor 80 (or the differential pressure reading) when no flow is generated through the device 12 via the expression $\Delta P_{Ref} + \text{TempCo}*(T_1 - T_{Ref})$. As such, the output of the differential pressure sensor 80 when no flow is generated through the device 12, or in other words, the differential pressure reading when there is no pressure drop, may be obtained or estimated using this expression without interrupting flow during therapy.

Methods 46 and 58 may be performed by processor 22 according to instructions (software code) stored therein. When processor 22 compensates the raw differential pressure reading for thermal drift according to instructions stored therein, such as in accordance with procedure 68 of method 58, this will be hereinafter referred to as "fine adjustment" or "fine correction."

Additional temperature compensation may be performed using pulse width modulation or coarse adjustment. During coarse adjustment, the signals that are inputted to the A-D converter 26 may be modified. Details of the coarse adjustment will be described below.

As mentioned earlier, differential pressure sensor 80 may be periodically auto-nulled. During this time, processor 22 may adjust the duty cycle of the pulse width modulated signals transmitted from the processor so that the high gain signals (signals received by the high gain channel from the processor) are essentially at mid-scale or "centered" on the A-D converter. This enables maximum symmetrical variation or swing (both positive and negative) on the high gain signal corresponding to positive and negative flows. In some embodiments, every time sensor 80 is auto-nulled, processor 22 searches for the duty cycle that enables the signals to be centered on the range of the A-D converter. This duty cycle may be "locked" or used as the default duty cycle. However, in some situations (at certain temperatures at or near the differential pressure sensor), the thermal drift may be so significant that the signals corresponding to the differential pressure reading may be shifted such that the signals are "railed" or driven against the power supply rail.

In such situations, the high gain channel may not provide useful readings. To mitigate this problem, processor 22 may be configured to calculate the temperature where such a shift would occur and accordingly, set the duty cycle of the pulse width modulated signals such that the signals would be properly re-centered on the range of the high gain channel or fit within the range of the high gain channel. For example, processor 22 may be able to calculate, based on the gain of fixed gain amplifier 44 and/or differential amplifier 42 and the resolution of the pulse width modulated signals, the number of A-D counts that the range of high gain flow signal can be shifted by changing the pulse width modulated signal by one count. Processor 22 may also be able to calculate the temperature at which the high gain flow signal would need to be shifted. Thus, processor 22 may increase or decrease the duty cycle of the pulse width modulated signal to "re-center" the high gain signal's range for input into high gain channel of the A-D converter 26. Processor 22 may be able to perform the coarse adjustment according to instructions stored therein.

In some embodiments, coarse adjustment may not be required for every raw differential pressure reading. For example, when the high gain signals are able to fit within the range of the high gain channel input, or in other words, the signals are not "railed," no adjustment of the duty cycle is necessary. As mentioned above, processor 22 may be able to calculate when adjustments are necessary. In contrast, fine adjustments may be performed every time a raw differential pressure reading is obtained. In some embodiments, during fine adjustment, processor 22 may perform procedure 68 of method 58 according to instructions stored in the processor to compensate the raw differential pressure reading for thermal drift by using at least the temperature compensation coefficient. During fine adjustment, temperature compensation may be applied to differential pressure values reflective of the signals received from both the high and low gain channels. In some situations, the amount of compensation applied to the differential pressure value received from the low gain channel may be insignificant (and essentially zero).

Figure 6:
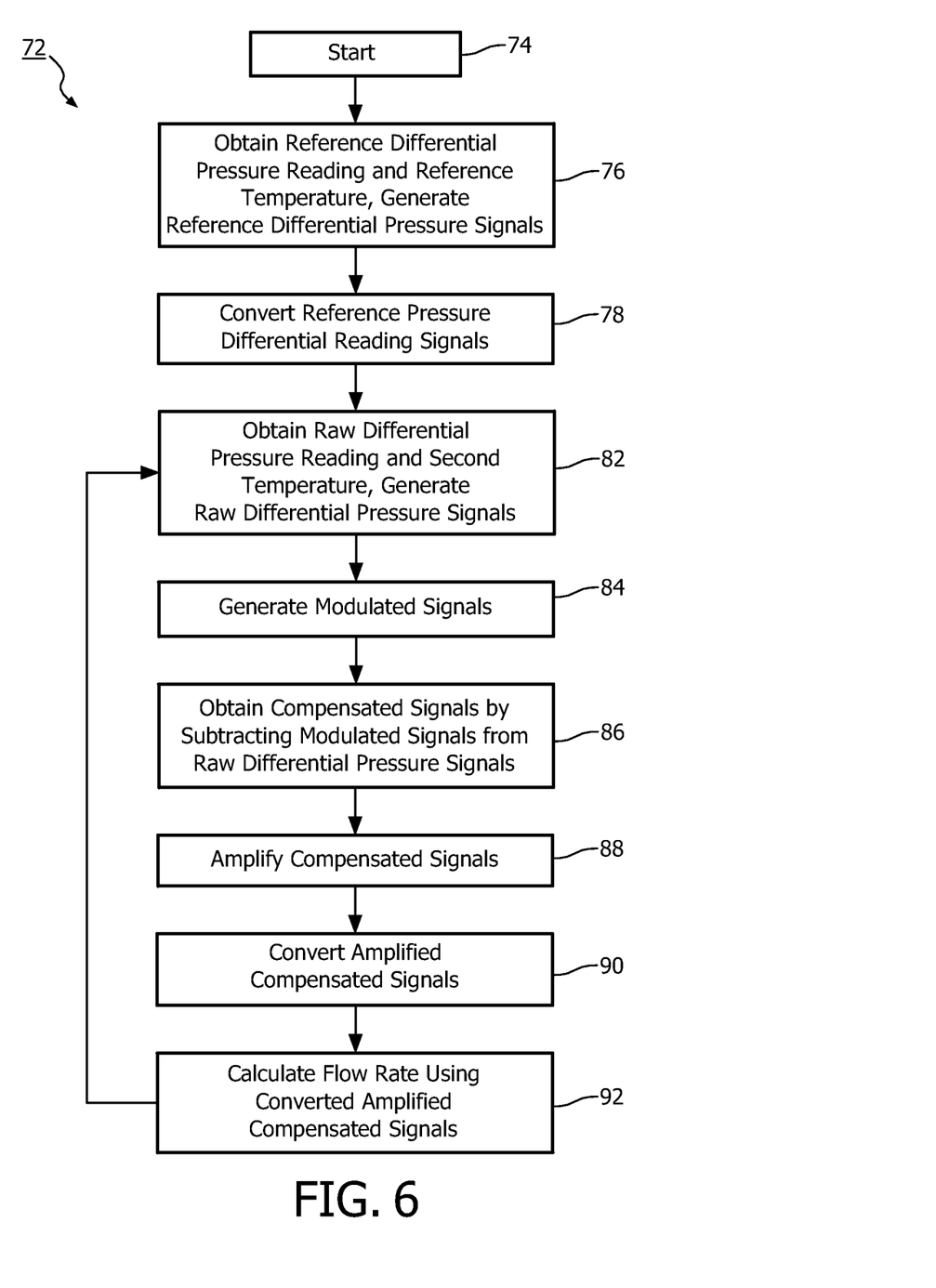
FIG. 6 illustrates a method of obtaining the flow rate using the device in accordance with the embodiment shown in FIG. 1.

FIG. 6 illustrates a method 72 of operation of device 12 in accordance with the embodiment shown in FIG. 1. Because method 58, as mentioned previously, describes the implementation of the temperature compensation coefficient to obtain the correct flow rate, method 58 may be performed when method 72 is performed. Method 72 starts at procedure 74 where flow is not yet generated through the device 12. At this procedure 74, a temperature compensation coefficient has already been obtained for device 12 and has been stored in the memory of the device. Method 72 then proceeds to procedure 76 where the reference differential pressure reading is obtained using the differential pressure sensor 80 and the reference temperature is obtained using temperature sensor 20. Differential pressure sensor 80 sends reference differential pressure signals reflective of the reference differential pressure reading to the A-D converter 26. Device 12 may auto-null the differential pressure sensor 80 during this procedure 76. During this procedure 76, processor 22 may also set the duty cycle of the pulse width modulated signals such that the signals are centered on the range of the high gain channel of the A-D converter.

Method 72 proceeds to procedure 78 where the reference differential pressure signals are converted from analog signals to digital signals by A-D converter 26 to be processed by processor 22. Flow may be generated through the device during or after this procedure 78. After flow is generated through the device 12, method 72 proceeds to procedure 82 where the raw differential pressure reading is obtained using differential pressure sensor 80 and the second temperature is obtained using the temperature sensor 20. Differential pressure sensor 80 generates raw differential pressure signals reflective of the raw differential pressure reading. The raw differential pressure signals are transmitted to the low gain channel of A-D converter 26 and differential amplifier 42.

Method 72 proceeds to procedure 84 where processor 22 determines whether the duty cycle of the pulse width modulated signals requires change and if so, the amount of change based on the temperature compensation coefficient, the second temperature, the reference temperature, and the reference differential pressure reading. Processor 22 may then change the duty cycle of the pulse width modulated signals transmitted to RC filter 40. RC filter 40 converts the digital signals into analog signals, as described previously. Although the signals outputted by RC filter 40 are now analog signals, it will also be referred to as pulse width modulated signals for simplicity.

Method 72 then proceeds to procedure 86 where the compensated differential pressure signals are obtained by subtracting the pulse width modulated signals from the raw differential pressure signals. The method 72 proceeds to procedure 88 where the compensated differential pressure signals are amplified by the fixed gain amplifier 44. In some embodiments, procedures 86 and 88 can be combined and performed by one differential amplifier 42.

Method 72 then proceeds to procedure 90 where the amplified compensated differential pressure signals are received by the high gain channel of A-D converter 26 and converted into digital signals for processing by processor 22. The raw differential pressure signal received by the low gain channel of A-D converter 26 is also converted into digital signals for processing by processor 22. The processor determines which signals to use—the signals received by the high gain channel or the signals received by the low gain channels, as described above. After processor 22 has determined which signals to use, the processor performs fine adjustment so that the differential pressure value obtained from either the high gain channel signals or the low gain channel signals (signals received by the low gain channel) can be compensated for thermal drift. The processor obtains the compensated differential pressure value, or the corrected differential pressure value, after performance of the fine adjustment. Processor 22 may perform fine adjustment in accordance with instructions stored therein.

When processor 22 performs fine adjustment to the differential pressure value reflective of the high gain signals, the processor may also factor in the adjusted duty cycle of the pulse width modulated signals to obtain the compensated differential pressure value. As mentioned above, this may be useful because the duty cycle of the pulse width modulated signals transmitted from processor 22 at procedure 84 may have been varied to "re-center" the pulse width modulated signals on the range of the high gain channel. Method 72 then proceeds to procedure 92 where processor 22 obtains the flow rate based on the compensated differential pressure value. Method 72 may also proceed back to procedure 82 to obtain the next raw differential pressure reading and temperature so as to continuously obtain the correct flow rate values for the device 12.

Figure 7:
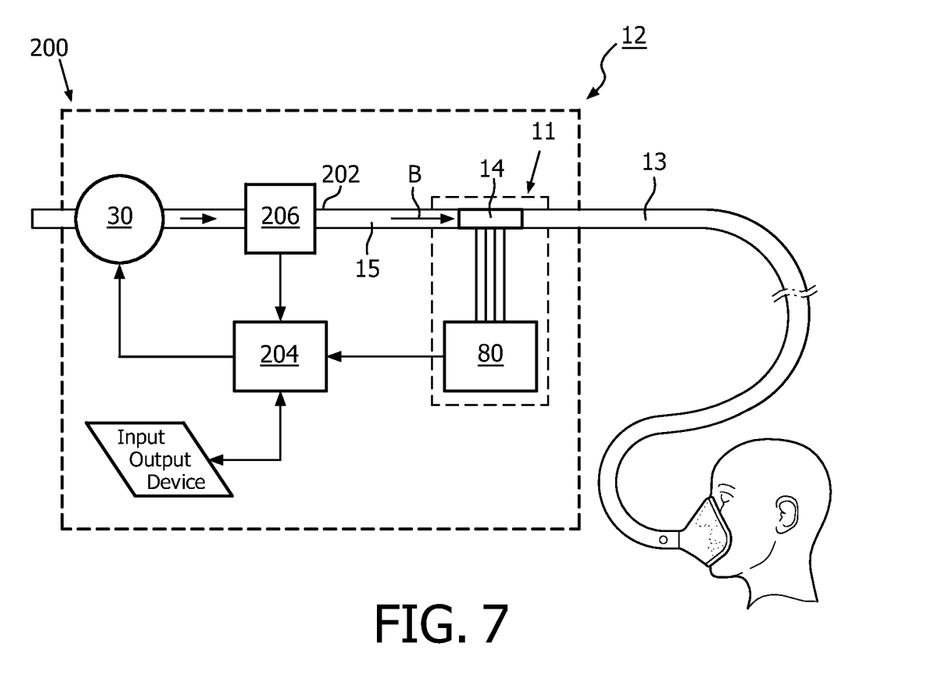
FIG. 7 is a schematic diagram illustrating the device in accordance with one embodiment.

FIG. 7 is a schematic diagram of device 12 in accordance with an embodiment. In this embodiment, the device is a CPAP device. The CPAP device may be of any kind, such as, for example, REMstar® family of CPAP devices manufactured by Philips Respironics. Device 12 includes a pressure generating system 200, that receives a supply of breathing gas from a breathing gas source, such as ambient atmosphere, and creates a flow of breathing gas at a pressure greater than ambient atmospheric pressure. The flow of breathing gas from pressure generator 30 is indicated by arrow B. The pressure generator 30, such as a blower, impeller, drag compressor, fan, piston, or bellows, or other device, then creates the flow of breathing gas at a pressure greater than the ambient atmospheric pressure. Pressure generator 30 is commonly a blower in which a fan or impeller is driven by a motor operating under the control of a controller 204, which is typically a processor capable of executing stored algorithms.

In some embodiments, controller 204 may be the same as microcontroller 28 and may include processor 22. An exit conduit 202 communicates the flow of breathing gas from an outlet of pressure generator 30. Other sensors 206 may be used in device 12 to sense conditions within the device 12 or characteristics of the flow (temperature, humidity, etc.). Flow sensing system 11 and the controller 204 may form part of the flow measuring system 10. Device 12 may obtain accurate flow measurements by compensating the differential pressure reading from the differential pressure sensor 80 using the temperature compensation coefficient. The device may obtain accurate flow measurements in accordance with methods 46, 58, and 72.

Embodiments of the invention may be made in hardware, firmware, software, or various combinations thereof. The invention may also be implemented as instructions stored on the processor. The processor may contain machine-readable medium or software, which may be read and executed using one or more processing devices or machines. The processor may include, for example, read only memory, random access memory, magnetic disk storage media, optical storage media, flash memory devices, and/or other media for storing information, and a machine-readable transmission media may include forms of propagated signals, including carrier waves, infrared signals, digital signals, and other media for transmitting information. While firmware, software, routines, or instructions may be described in the above disclosure in terms of specific exemplary aspects and embodiments performing certain actions, it will be apparent that such descriptions are merely for the sake of convenience and that such actions in fact result from computing devices, processing devices, processors, controllers, or other devices or machines executing the firmware, software, routines, or instructions.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A medical breathing apparatus configured to calculate a flow rate within the medical breathing apparatus, wherein the medical breathing apparatus uses a temperature coefficient that is recalibrated for the medical breathing apparatus, the medical breathing apparatus comprising:
   a flow path;
   a flow restriction portion disposed in the flow path, wherein the flow restriction portion creates a differential pressure within the flow path;
   a differential pressure sensor configured to generate a first differential pressure signal conveying information related to the differential pressure within the flow path, wherein the differential pressure sensor is further configured to generate a second differential pressure signal conveying information related to the differential pressure within the flow path;
   a temperature sensor configured to generate a first temperature signal conveying information related to a first temperature at or near the differential pressure sensor, wherein the temperature sensor is further configured to generate a second temperature signal conveying information related to a second temperature at or near the differential pressure sensor, the second temperature signal indicating heating of the differential pressure sensor caused by flow through the medical breathing apparatus; and
   a processor configured to:
     determine a first differential pressure parameter based on the first differential pressure signal;
     determine a second differential pressure parameter based on the second differential pressure signal, wherein a pressure drop across the flow restriction portion during the first differential pressure parameter determination is the same as a pressure drop across the flow restriction portion during the second differential pressure parameter determination;
     determine the first temperature based on the first temperature signal, wherein the first temperature is determined prior to a commencement of operation of the medical breathing apparatus;
     determine the second temperature based on the second temperature signal, wherein the second temperature is determined subsequent to a cessation of operation of the medical breathing apparatus;
     determine a temperature coefficient by dividing a difference between the second differential pressure parameter and the first differential pressure parameter by a difference between the second temperature and the first temperature;

determine a compensated differential pressure parameter by determining a difference between a raw differential pressure value and compensation value determined based on the temperature coefficient, wherein the compensated differential pressure parameter compensates for thermal drift caused by flow through the medical breathing apparatus;

pulse width modulate signals conveying information related to the compensated differential pressure parameter for transmission through a differential amplifier, the differential amplifier being configured to generate an amplified differential pressure parameter based on the pulse width modulated signals;

convert, via an A-D converter, the amplified differential pressure parameter into a converted differential pressure parameter, the A-D converter having a high gain channel configured to receive the amplified differential pressure parameter;

responsive to a temperature value breaching a predetermined threshold, adjust a range of the high gain channel; and determine the flow rate within the medical breathing apparatus based on the converted differential pressure parameter.

2. The medical breathing apparatus of claim 1, wherein the medical breathing apparatus is a continuous positive airway pressure device, or a ventilator.

3. The medical breathing apparatus of claim 1, further comprising a D-A converter configured to convert digital signals from the processor into analog signals to be received by the differential amplifier.

4. The medical breathing apparatus of claim 1, further comprising an RC filter configured to convert digital signals from the processor into analog signals to be received by the differential amplifier.

5. The medical breathing apparatus of claim 4, wherein the processor transmits the pulse width modulated signals to the RC filter, and wherein the differential amplifier receives an average of the pulse width modulated signals from the RC filter.

6. The medical breathing apparatus of claim 1, wherein the A-D converter further includes a low gain channel, and wherein the processor is further configured to select between the high gain channel and the low gain channel based on whether the flow rate is below a predetermined threshold.

7. The medical breathing apparatus of claim 1, wherein the medical breathing apparatus is configured to hold an air pressure in a user's airway at one atmosphere.

8. A method for calculating a flow rate within a medical breathing apparatus, wherein the medical breathing apparatus uses a temperature coefficient that is pre-calibrated for the medical breathing apparatus, the medical breathing apparatus comprising a flow path, a flow restriction portion, a differential pressure sensor, a temperature sensor, a processor, an A-D converter, and a differential amplifier, the method comprising:

creating, by the flow restriction portion, a differential pressure within the flow path;

generating, by the differential pressure sensor, a first differential pressure signal conveying information related to the differential pressure within the flow path;

generating, by the differential pressure sensor, a second differential pressure signal conveying information related to the differential pressure within the flow path;

generating, by the temperature sensor, a first temperature signal conveying information related to a first temperature at or near the differential pressure sensor;

generating, by the temperature sensor, a second temperature signal conveying information related to a second temperature at or near the differential pressure sensor, the second temperature signal indicating heating of the differential pressure sensor caused by flow through the medical breathing apparatus;

determining, by the processor, a first differential pressure parameter based on the first differential pressure signal;

determining, by the processor, a second differential pressure parameter based on the second differential pressure signal, wherein a pressure drop across the flow restriction portion during the first differential pressure parameter determination is the same as a pressure drop across the flow restriction portion during the second differential pressure parameter determination;

determining, by the processor, the first temperature based on the first temperature signal, wherein the first temperature is determined prior to a commencement of operation of the medical breathing apparatus;

determining, by the processor, the second temperature based on the second temperature signal, wherein the second temperature is determined subsequent to a cessation of operation of the medical breathing apparatus;

determining, by the processor, a temperature coefficient by dividing a difference between the second differential pressure parameter and the first differential pressure parameter by a difference between the second temperature and the first temperature;

determining, by the processor, a compensated differential pressure parameter by determining a difference between a raw differential pressure value and compensation value determined based on the temperature coefficient, wherein the compensated differential pressure parameter compensates for thermal drift caused by flow through the medical breathing apparatus;

pulse width modulating, by the processor, signals conveying information related to the compensated differential pressure parameter for transmission through the differential amplifier, the differential amplifier being configured to generate an amplified differential pressure parameter based on the pulse width modulated signals;

converting, by the A-D converter, the amplified differential pressure parameter into a converted differential pressure parameter, the A-D converter having a high gain channel configured to receive the amplified differential pressure parameter;

responsive to a temperature value breaching a predetermined threshold, adjusting, by the processor, a range of the high gain channel; and determining, by the processor, the flow rate within the medical breathing apparatus based on the converted differential pressure parameter.

9. The method of claim 8, further comprising holding, with the medical breathing apparatus, an air pressure in a user's airway at one atmosphere.

* * * * *